United States Patent
Yan et al.

(10) Patent No.: US 9,561,485 B2
(45) Date of Patent: Feb. 7, 2017

(54) SUSTAINED RELEASE SILICA MICROCAPSULES

(75) Inventors: Laibin Bruce Yan, Lansdale, PA (US); Craig Arlen Martin, Morrisville, PA (US); Raed Abu-Reziq, Jatt Hamesholash (IL)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

(21) Appl. No.: 13/515,166

(22) PCT Filed: Dec. 6, 2010

(86) PCT No.: PCT/US2010/059102
§ 371 (c)(1),
(2), (4) Date: Aug. 8, 2012

(87) PCT Pub. No.: WO2011/081787
PCT Pub. Date: Jul. 7, 2011

(65) Prior Publication Data
US 2012/0295790 A1 Nov. 22, 2012

Related U.S. Application Data

(60) Provisional application No. 61/286,535, filed on Dec. 15, 2009.

(51) Int. Cl.
*A61K 9/50* (2006.01)
*B01J 13/18* (2006.01)
*A01N 25/28* (2006.01)
*B01J 13/20* (2006.01)

(52) U.S. Cl.
CPC .............. *B01J 13/185* (2013.01); *A01N 25/28* (2013.01); *B01J 13/20* (2013.01)

(58) Field of Classification Search
None
See application file for complete search history.

(56) References Cited

U.S. PATENT DOCUMENTS

| | | | |
|---|---|---|---|
| 3,785,798 A | 1/1974 | Horai et al. | |
| 4,464,317 A | 8/1984 | Thies et al. | |
| 4,931,362 A | 6/1990 | Zsifkovits et al. | |
| 6,132,773 A | 10/2000 | Amiche | |
| 6,303,149 B1 | 10/2001 | Magdassi et al. | |
| 2007/0292676 A1 | 12/2007 | Naigertsik | |
| 2008/0199523 A1 | 8/2008 | Finnie et al. | |
| 2008/0254082 A1* | 10/2008 | Toledano et al. | 424/408 |
| 2009/0081262 A1* | 3/2009 | Toledano et al. | 424/401 |

FOREIGN PATENT DOCUMENTS

| | | |
|---|---|---|
| JP | 2002066307 A | 3/2002 |
| WO | 03/066209 A1 | 8/2003 |
| WO | 2010/013250 A2 | 2/2010 |

OTHER PUBLICATIONS

Hu et al.(Synthesis of Novel Nickel Hollow Nanospheres, Chinese J. of Inorganic Chemistry, vol. 22 No. 2, pp. 293-297, 2006).*
Zhang et al.(Synthesis of Submicrometer-Sized Hollow Silver Spheres in Mixed Polymer-Surfactant Solutions, Adv. Mater., 2002,14 No. 20, pp. 1499-1501.*
Wang et al., Synthesis and characterization of Cu3P hollow spheres by a facile soft-template process, Journal of Alloys and Compounds 474 (2009) 233-236.*
Examination Report for Canada Application No. 2,783,245, mailed Sep. 19, 2016.

* cited by examiner

*Primary Examiner* — Alton Pryor
(74) *Attorney, Agent, or Firm* — Hauptman Ham, LLP

(57) ABSTRACT

The present invention relates to a microcapsule exhibiting desirable sustained-release properties, which microcapsule comprises a core material comprising an active ingredient encapsulated within a silica shell, characterized in that the outer surface of such silica shell has a layer of a metal selected from Group 2a, Group 8, Group 2b or Group 3a of the Periodic Table bound thereto. In other aspects this invention relates to a method of making such a microcapsule; a pesticidal composition comprising microcapsules comprising a pesticidal active ingredient and a suitable carrier; and to a method of controlling pests comprising applying an effective amount of such a pesticidal composition to a locus where pests are or are expected to be present.

14 Claims, 1 Drawing Sheet

US 9,561,485 B2

SUSTAINED RELEASE SILICA MICROCAPSULES

FIELD OF THE INVENTION

The present invention relates to treated microcapsules exhibiting desirable sustained-release properties. The invention also relates to a method of making treated microcapsules.

BACKGROUND OF THE INVENTION

In many fields, particularly the agricultural chemical field, it is highly desirable to produce compositions which provide a controlled release of an active ingredient. Such compositions can provide desirable control of pests with less frequent and/or lower application rates of pesticides as the active ingredient will be released over a period of time.

Among the approaches taken in the past to provide such controlled release has been the incorporation of the active ingredient into a microcapsule. In the past, such microcapsules have typically been composed of organic polymers such as polyureas. However, due to the presence of polyisocyanates in the core material, such polyurea technology may not be useful with many pesticides (See U.S. Patent Application Publication No. 2008/0254082). Moreover, the use of such organic polymers may not be desirable in some circumstances from an environmental perspective.

In order to overcome these limitations, it has been proposed to encapsulate pesticides in a silica shell employing a sol gel emulsion polymerization process. Thus, for example, U.S. Patent Application Publication No. 2008/0254082 discloses the use of silica microencapsulated pesticides to achieve controlled release such that extended residual activity is observed. Somewhat similarly, U.S. Pat. No. 6,303,149, U.S. Patent Application Publication No. 2007/0292676 and U.S. Patent Application Publication No. 2008/0199523 all disclose sol gel processes for the encapsulation of active ingredients (including pesticides) in non-modified silica shells.

Although such silica microcapsules provide a degree of sustained release, it would be desirable to produce compositions which provide enhanced residual activity, and yet which maintain the benefits of such silica microcapsules.

PCT Application WO 03/066209 discloses an encapsulation process and composition for cosmetic active materials (particularly sunscreens) which can be skin irritants and which therefore should be formulated such that they do not come into contact with the skin. This publication indicates that sol gel produced silica shells can be made more impermeable by post-treatment with a Group IVB, IVA or VA metal alkoxy or acyloxy compound. While such highly impermeable shells are desirable for encapsulating actives which should be maintained within the shell wall, they are not useful for active ingredients—such as pesticides—which must be released from the shells in order to be effective. Accordingly, one would conclude from a reading of WO 03/066209 that post-treating sol gel produced silica shells with a metal would render them too impermeable for use as an effective pesticide encapsulant.

SUMMARY OF THE INVENTION

In one aspect, the present invention relates to a treated microcapsule exhibiting desirable sustained-release properties, which treated microcapsule comprises a core material comprising an active ingredient encapsulated within a silica shell having an outer surface, characterized in that the outer surface of the silica shell has bound thereto a layer of a metal, the metal comprising a metal selected from the group consisting of Group 2a, Group 8, Group 2b or Group 3a metals of the Periodic Table.

In another aspect, this invention relates to a method of making such a treated microcapsule, comprising the steps of:
a) encapsulating a core material in a silica shell employing a sol gel polymerization process to form a microcapsule; and
b) treating such microcapsule with an inorganic acid or salt of a metal selected from Group 2a, Group 8, Group 2b or Group 3a metals of the Periodic Table.

In a further aspect, this invention is directed to a pesticidal composition comprising:
a) a treated microcapsule comprising an active ingredient which is a pesticide; and
b) a carrier.

In yet another aspect, this invention is directed to method of controlling pests comprising applying an effective amount of such a pesticidal composition to a locus where pests are or are expected to be present.

DETAILED DESCRIPTION OF THE INVENTION

Figure 1:
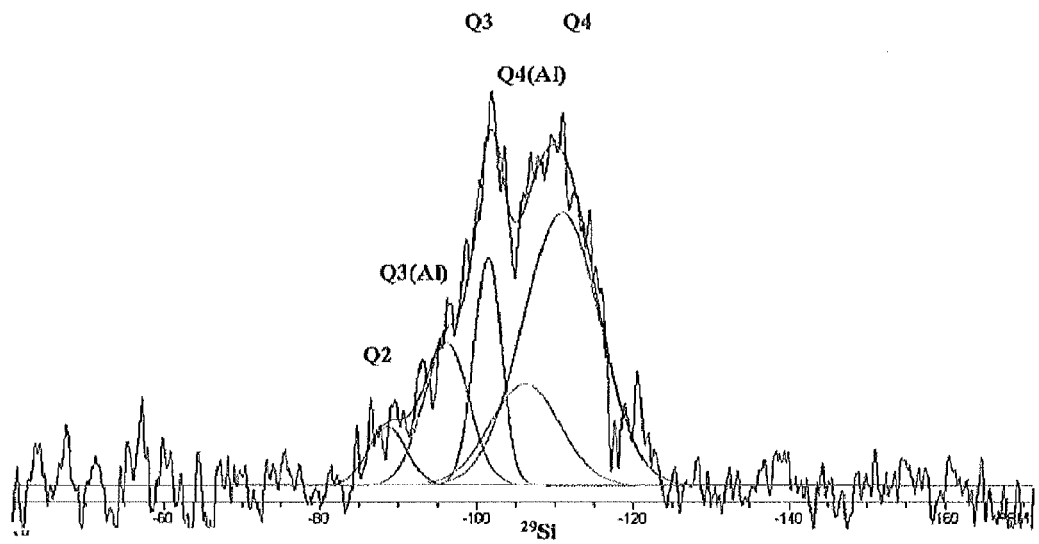
FIG. 1 is an NMR spectrum of a microcapsule of this invention which has been post-treated with aluminum sulfate, which spectrum has been deconvoluted to quantify Si—O—Si and Si—O—Al interactions.

In one aspect, the present invention relates to a treated microcapsule exhibiting desirable sustained-release properties, which treated microcapsule comprises a core material comprising an active ingredient encapsulated within a silica shell having an outer surface, characterized in that the outer surface of the silica shell has bound thereto a layer of a metal, the metal comprising a metal selected from the group consisting of Group 2a, Group 8, Group 2b or Group 3a metals of the Periodic Table.

As employed herein, the term "core material" refers to the inside part of the microcapsules comprising the active ingredient that is surrounded by the shell of the microcapsules. The core material refers to both the active ingredient and any optional excipients such as a liquid carrier used to dissolve or disperse the active ingredient.

As employed herein, the term "microcapsule" refers to a composition comprising a core material encapsulated by a silica shell which has not been modified by post-treatment with an inorganic Group 2a, Group 8, Group 2b or Group 3a metal salt or acid.

As employed herein, the term "treated microcapsule" refers to a composition comprising a core material encapsulated by a silica shell which has been modified by post-treatment with an inorganic Group 2a, Group 8, Group 2b or Group 3a metal salt or acid.

The active ingredient may comprise any material which is dispersible or soluble in the silica precursors employed in the sol-gel polymerization process used to create the silica microcapsules which are subsequently post-treated to produce the microcapsules of this invention; and which does not decompose under the reaction conditions employed. Preferably, such active ingredient is substantially water insoluble, having a solubility in water of less than about 0.5% w/w, typically less than about 0.25% w/w and at times less than about 0.1% w/w at room temperature (20° C.).

Preferably, the active ingredient is a pesticide. As is employed herein the term "pesticide" refers to a molecule or combination of molecules that repels, retards, or kills pests, such as, but not limited to, deleterious or annoying insects, weeds, worms, fungi, bacteria, and the like, and can be used especially for crop protection, but also for other purposes such as edifice protection; turf protection; pesticide as used herein includes, but is not limited to insecticides, acaricides, fungicides, herbicides, nematicides, ectoparasiticides, and growth regulators, either used to encourage growth of a desired plant species or retard growth of an undesired pest.

Preferably the concentration of the pesticide based on the total weight of the core material is in the range of between about 2 and about 100% w/w; more preferably between about 10 and about 100% w/w; and is most preferably in the range of between about 20 and about 100% w/w.

Illustrative herbicides which may be employed include Acetochlor, Aclonifen, Alachlor, Anilofos, Asulam, Benfluralin, Benfuresate, Bensulide, Benzoylprop-ethyl, Bromoxynil, Butachlor, Butenachlor, Butralin, Carfentrazone-ethyl, Chlorbufam, Chlorfenprop-methyl, Chlorpropham, Clodinafop-propargyl, Clofop-isobutyl, Clomazone, Cloquintocet-methyl, Cycloxydim, Cyometrinil, Di-allate, Diclofop-methyl, Diethatyl-ethyl, Diflufenican, Dimepiperate, Dimethachlor, Dimethametrin, Dimethenamid-P, Dinoseb, Ethalfluralin, Ethofumesate, Ethoxysulfuron, Fenoxaprop, Fenthiaprop-ethyl, Fentrazamide, Fluazifop-butyl, Fluazifop-P-butyl, Fluchloralin, Fluoroglycophen-ethyl, Fluorochloridone, Fluoroxypyr-methyl, Haloxyfop-P-methyl, Idosulfuron, Ioxynil Octanoate, Lactofen, MCPB-ethyl, Mesotrionc, Methoxyphenone, Metolachlor, Metribuzin, Nitrofen, Nonanoic Acid, Orbincarb, Oxadiazon, Pendimethalin, Pethoxamid, Phenmedipham, Pinoxaden, Propaquizofop, Propischlor, Pyridate, Pyriftalid, Quinoline, Quizalofop-tefuryl, S-metolachlor, Thiobencarb, Tri-allate, Tridifane, Trifloxysulfuron sodium, Trifluralin and mixtures of any of the above.

Representative insecticides include Abamectin, Aldicarb, Aldrin, Alpha-cypermethrin, Avermectin, Azinphos-ethyl, Beta-cyfluthrin, Beta-cypermethrin, Bifenthrin, Bioremethrin, Bromophos, Bufencarb, Buprofezin, Carbofuran, Carbaryl, Chlorfenvinphos, Chlorphoxim, Chlorpyrifos, Chlorpyriphos-methyl, Clofentezine, Cyfluthrin, Cypermethrin, Cyromazine, DDVP, Deltamethrin, Diafenthiuron, Dialifos, Diazinon, Dicofol, Dimethoate, Dimethomorph, Dimethylvinphos, Dioxabenzofos, Disulfoton, Emamectin benzoate, EPN, Endosulfan, Esfenvalerate, Ethiofencarb, Etofenprox, Fenamiphos, Fenchlorphos, Fenitrothion, Fenobucarb, Fenoxycarb, Fenpropathrin, Fensulfothion, Fenvalerate, Fipronil, Flufenoxuron, Fosmethilan, Fosthiazate, Gamma-cyhalothrin, Imidacloprid, Isoprocarb, Ivermectin, Lambda-cyhalothrin, Lufenuron, Malathion, Mecarphon, Methamidofos, Methidathion, Methomyl, Metolcarb, Monocrotophos, Niclosamide, Novaluron, Parathion, Permethrin, Phenthoate, Phorate, Phoxim, Pirimiphos-ethyl, Pirimicarb, Profenofos, Propoxur, Prothoate, Pymetrozin, Sulprofos, Tetramethrin, Thiamethoxam, Thiacloprid, Thiodicarb, Thionazin, Transfluthrin, Triazamate, Tribufos, Triflumuron, Zeta-cypermethrin and mixtures of any of the above.

Fungicides which may be employed include Aldimorph, Azoxystrobin, Binapacryl, Buthiobate, Captan, Chlorothalonil, Cyflufenamid, Cyproconazole, Difenoconazole, Diflumetorim, Dinobuton, Dinocap, Dedemorph acetate, Edifenphos, Epoxiconazole, Etridiazole, Fenamidon, Fenpropimorph, Fenitropan, Flusilazole, Folpet, Furalaxyl, Furmtecyclox, Imazalil, Isoprothiolane, Kresoxim-methyl, Mefenoxam, Metominostrobin, Nitrothal-isopropyl, Penconazole, 2-Phenylphenol, Propiconazole, Prochloraz, Proquinazid, Prothioconazole, Pyraclostrobin, Pyrazophos, Pyrimethanil, Qyprodinil, Tebuconazole, Tetraconazole, Thiabendazole, Triadiminol, Trifloxystrobin Triticonazole and mixtures of any of the above.

The outer surface of the silica shell of the microcapsules of this invention has a layer of a metal selected from Group 2a, Group 8, Group 2b or Group 3a of the Periodic Table bound thereto. Such layer may be continuous or discontinuous.

Preferably, such metal is selected from the group consisting of calcium, magnesium, iron, nickel, copper, boron and aluminum. Most preferably, such metal is aluminum.

In another aspect, the present invention is directed to a process for making a treated microcapsule comprising the steps of:

a) encapsulating a core material in a silica shell employing a sol gel polymerization process to form a microcapsule; and b) treating the microcapsule with an inorganic acid or salt of a metal selected from Group 2a, Group 8, Group 2b or Group 3a of the Periodic Table.

Sol gel polymerization processes for the encapsulation of core materials in a silica shell are well known in the art, and are described in, for example, U.S. Pat. No. 6,303,149, U.S. Patent Application Publication No. 2007/0292676, U.S. Patent Application Publication No. 2008/0254082, U.S. Patent Application Publication No. 2008/0199523 and PCT Application WO 03/066209, the disclosures of which are hereby incorporated by reference. Any of such procedures may be employed to produce microcapsules in accordance with step (a) of the process of this invention.

According to a preferred embodiment of the present invention, the silica shell is produced by a sol gel process comprising the in-situ polymerization of silicon alkoxide monomers having the formula $Si(OR)_4$ where R is $C_1$-$C_6$ alkyl. As used herein the term "in-situ polymerization" refers to the sol gel polymerization process of sol gel precursors to form a silica shell at the oil-water interface of an emulsion as a result of the hydrolysis and condensation reactions of the sol gel precursors.

Additionally according to a preferred embodiment of the present invention, the silicon alkoxide monomer is selected from tetramethoxy silane, tetraethoxy silane, and mixtures thereof.

The precursor (silicon alkoxide monomer) may be a single monomeric unit or alternatively the precursor may be comprised of a number of monomeric units. For example, the precursor may be an oligomer of the precursor for example, a prehydrolyzed tetraethoxy silane (TEOS) which is based on the hydrolysis of TEOS, which may be used in order to obtain short chain polymers that can also be used for encapsulation.

Most preferably the silicon alkoxide monomer or oligomer forms a pure silica shell (i.e. not an organically modified silica).

The process of the present invention is based on the preparation of an oil-in-water emulsion by emulsifying a hydrophobic solution (oily phase) that comprises the precursors and the core material comprising the at least one active ingredient (preferably a pesticide), in aqueous solution, with or without the need for mixing the emulsion with another aqueous solution to accelerate the condensation-polymerization reaction.

According to a preferred embodiment of the present invention, the microcapsules are prepared by a process comprising preparing an oil-in-water emulsion by emulsification of a water insoluble liquid phase comprising a water insoluble silicon alkoxide monomers having the formula $Si(OR)_4$ where R is $C_1$-$C_6$ alkyl and the core material, in an aqueous phase comprising an aqueous solution having a pH in the range of between about 2 and about 13, under appropriate shear forces and temperature conditions. More preferably, the pH is in the range of between about 2 and about 7. The process may further comprise mixing and stirring the emulsion obtained with an aqueous solution having a pH in the range of between about 2 and about 13 to obtain microcapsules in a suspension.

Preferably, the weight ratio of the silicon alkoxide monomers to the core material is in the range of between about 3:97 and about 30:70; more preferably in the range of between about 3:97 and about 15:85.

The particle size of the microcapsules may be in the range of between about 0.01 and about 1000 μm in diameter; is preferably between about 0.1 and about 100 μm in diameter; and is more preferably between about 1 and about 10 μm in diameter.

In step b of the process of this invention, the microcapsules produced in step a are treated with an inorganic Group 2a, Group 8, Group 2b or Group 3a metal salt or acid. Preferred salts include chlorides, nitrates and sulfates. Preferred reactants include aluminum chloride, aluminum nitrate, boric acid, iron chloride, zinc sulfate and aluminum sulfate; with aluminum sulfate and aluminum chloride being particularly preferred.

According to a preferred embodiment of step b of the process of the present invention, the microcapsule suspension produced in step a is diluted with water. This mixture is stirred until uniform and an aqueous sodium alkylsulfate solution is added. The following reagents are added with good agitation during and between each addition step: aqueous metal salt solution; an aqueous polyvinyl alcohol solution; and an aqueous sodium silicate solution. The resultant slurry contains the metal treated silica capsules containing at least one active ingredient.

The preferred amounts of diluents and reagents employed in step b, relative to the microcapsule suspension produced in step are as follows:

It is preferred that the microcapsule suspension produced in step a be diluted with enough water to make a mixture that can be stirred easily. The amount of water needed to produce such a mixture is in an amount of from about 25% to about 50% by weight as compared to the microcapsule suspension weight, preferably from about 30% to about 35% by weight.

The alkyl group of sodium alkylsulfate preferably contains from 6 to 18 carbon atoms, and most preferably from 10 to 12 carbon atoms. This compound is preferably present in an amount of from about 0.25% to about 2.0% by weight, and is more preferably present at between about 0.5% and about 1.0% by weight, based upon the weight of the microcapsule suspension.

The aqueous metal salt solution is added to give a molar ratio of silica to metal oxide in the metal-treated silica shell wall of preferably from about 5:1 to about 15:1, more preferably of from about 8:1 to about 10:1, moles silica: moles metal oxide.

It is preferred that the polyvinyl alcohol is diluted with water prior to its addition for ease of handling, but this is not necessary for the procedure. The amount of polyvinyl alcohol present in the metal treated capsule slurry is preferably from about 1.0% to about 2.0% by weight, more preferred is 1.4% to 1.6% by weight, based upon the weight of the microcapsule suspension.

The aqueous sodium silicate solution is preferably a 10.0% to 30.0% solution of sodium silicate added in an amount of from about 1.0% to about 10.0% by weight, more preferably from about 5.0 to about 6.0% by weight, based upon the weight of the microcapsule suspension.

The pesticidal composition of this invention comprises:
a) a treated microcapsule comprising an active ingredient which is a pesticide; and
b) a carrier.

Preferably, the carrier is an aqueous-based carrier. More preferably, the carrier is water; which may additionally include additives such as dispersing/wetting agents, viscosity imparting agents, and the like.

The treated microcapsules may be employed in the form of mixtures with a solid, semi solid or liquid dispersible carrier vehicles and/or other known compatible active agents such as other pesticides, or fertilizers, growth-regulating agents, etc., if desired, or in the form of particular dosage preparations for specific application made therefrom, such as solutions, emulsions, suspensions, powders, pastes, foams, tablets, polymeric sheets, aerosols, etc. and which are thus ready for use. Preferably the preparation is in the form of a suspension of the treated microcapsules in an aqueous medium.

In another aspect, this invention is directed to a method of controlling pests comprising applying an effective amount of the pesticidal compositions described above to a locus where pests are or are expected to be present. The amounts and locations of such application will depend upon the particular active ingredient employed and the pest to be controlled. However, one of ordinary skill in the art could readily determine such amounts employing means well known to those of skill in the art. Due to the improved controlled release of active ingredient exhibited by the compositions of this invention, such compositions can provide desirable control of pests with less frequent and/or lower application rates.

EXAMPLES

Example 1 and Comparative Experiment A

A. Example 1

Preparation of Alumina Treated Silica Capsules Containing Chlorpyrifos a) Preparation of Silica Capsules Containing Chlorpyrifos Into a 5 liter mixing vessel, fitted with a mechanical stirrer, were added 1,200.03 grams of an aqueous 1% cetyltrimethyl ammonium chloride solution. The solution was stirred at room temperature.

Into a 3 liter mixing vessel, fitted with a mechanical stirrer, were added 94.50 grams of refined paraffinic petroleum oil (Sunspray® 6N, available from Sunoco, Inc) and 31.62 grams of heavy aromatic naphtha (Aromatic 200, available from ExxonMobil chemical Company), 5.49 grams of epoxidized soybean oil, 2.40 grams of octanal, 180.14 grams of tetraethyl orthosilicate and 286.62 grams of warm (50° C.) chlorpyrifos technical (95.0% purity). This mixture was stirred until uniform.

The contents of the second vessel were added slowly to the first vessel with continued stirring. Once the addition was complete the mixture was homogenized for 1.5 minutes at 6500 RPM using a Polytron 6100 high-shear mixer. A particle size of less than 8 microns at D 90 was achieved. The mixture was transferred to a jacketed, 3 liter reactor vessel fitted with an overhead mechanical stirrer, warming the stirring mixture to 40° C. With continued stirring, 1,200.6 grams of a 0.0005N hydrochloric acid solution was added. Upon complete addition, the resultant mixture stirred at 40° C. for about 20 hours. The mixture was cooled to about 25° C. and was transferred portion wise into centrifuge bottles and centrifuged at 3500 RPM for 30 minutes. The supernatant was removed from each centrifugation, collecting the silica encapsulated chlorpyrifos as a wet cake for a total of 549.4 grams.

b) Preparation of Aluminum Cross-linked Silica Capsules Containing Chlorpyrifos

Into a mixing vessel fitted with a mechanical stirrer were added 229.71 grams of deionized water and 3.83 gram of sodium decyl sulfate (Polystep® B-25 available from Stepan Corporation). This mixture was stirred until a solution formed. To this solution were added 536.00 grams of the silica encapsulated chlorpyrifos wet cake prepared in Step a, stirring the mixture until the slurry was uniform. An aqueous 3% aluminum sulfate solution (122.51 grams) was added slowly, and after complete addition, stirring was continued for about 10 minutes. An aqueous 33% polyvinyl alcohol solution, 22.97 grams, (Celvol® 24-203, available from Sekisui Specialty Chemicals) was added drop wise and after complete addition, the mixture was stirred for about 2 minutes. An aqueous 14% sodium silicate solution, 30.63 grams, was added very slowly while maintaining good agitation and, after complete addition, the mixture was stirred for about 2 hours. The resultant slurry provided 915.03 grams of alumina treated silica capsules containing chlorpyrifos. A sample of the slurry was analyzed by HPLC and found to contain 28.3% chlorpyrifos (wt %).

c) Freeze Drying of Alumina Treated Capsules Containing Chlorpyrifos

The slurry produced in Step b was poured into a 600 mL VirTis drying flask. The flask was placed into a dry ice-acetone bath and kept there until the slurry froze. The flask containing the frozen slurry was transferred to a VirTis freeze drier (available from SP Industries) and was vacuum freeze dried at minus 80° C. for 24 hours. The drying flask was removed from the freeze drier and allowed to warm to room temperature. The contents of the drying flask were removed and stored in a clean glass container.

B. Comparative Experiment A

Preparation of Silica Capsules Containing Chlorpyrifos

Into a 5 liter mixing vessel, fitted with a mechanical stirrer, were added 1,200.3 grams of an aqueous 1% cetyl-trimethyl ammonium chloride solution. The solution was stirred at room temperature.

Into a 3 liter mixing vessel, fitted with a mechanical stirrer, were added 94.59 grams of refined paraffinic petroleum oil (Sunspray® 6N, available from Sunoco, Inc) and 31.52 grams of heavy aromatic naphtha (Aromatic 200, available from ExxonMobil Chemical Company), 5.5 grams of epoxidized soybean oil, 2.42 grams of octanal, 180.11 grams of tetraethyl orthosilicate and 287.4 grams of warm (50° C.) chlorpyrifos technical (95.0% purity). This mixture was stirred until uniform.

The contents of the second vessel were added slowly to the first vessel with continued stirring. Once the addition was complete the mixture was homogenized for 1.5 minutes at 6500 RPM using a Polytron 6100 high-shear mixer. A particle size of less than 8 microns at D 90 was achieved. The mixture was transferred to a jacketed, 3 liter reactor vessel fitted with an overhead mechanical stirrer, warming the stirring mixture to 40° C. With continued stirring, 1,200.0 grams of a 0.0005N hydrochloric acid solution was added. Upon complete addition, the resultant mixture stirred at 40° C. for about 20 hours. The mixture was cooled to about 25° C. and was transferred portion wise into centrifuge bottles and centrifuged at 3500 RPM for 30 minutes. The supernatant was removed from each centrifugation, collecting the silica encapsulated chlorpyrifos as a wet cake for a total of 416.0 grams.

C. NMR Evaluation

An NMR evaluation of the samples produced in Example 1 and Comparative Experiment A was undertaken as follows. Solid-state $^1$H MAS, $^{29}$Si MAS with $^1$H decoupling, and $^1$H->$^{29}$Si CPMAS NMR experiments were performed at 25° C. on a Bruker A VIII 300 (7.0 T) using a 4 mm CP MAS probe at a spinning speed of 3.0 ($^1$H) and 2.5 ($^{29}$Si) kHz. Each sample was packed directly into a 4 mm Bruker zirconia rotor. $^1$H and $^{29}$Si chemical shifts were referenced to an external standard of tetramethyl silane 0.0 ppm and tetrakis(trimethylsilyl)silane at −10 ppm, respectively. Spectral deconvolution was performed using NUTS software available from Acorn NMR, Inc.

Figure 2:
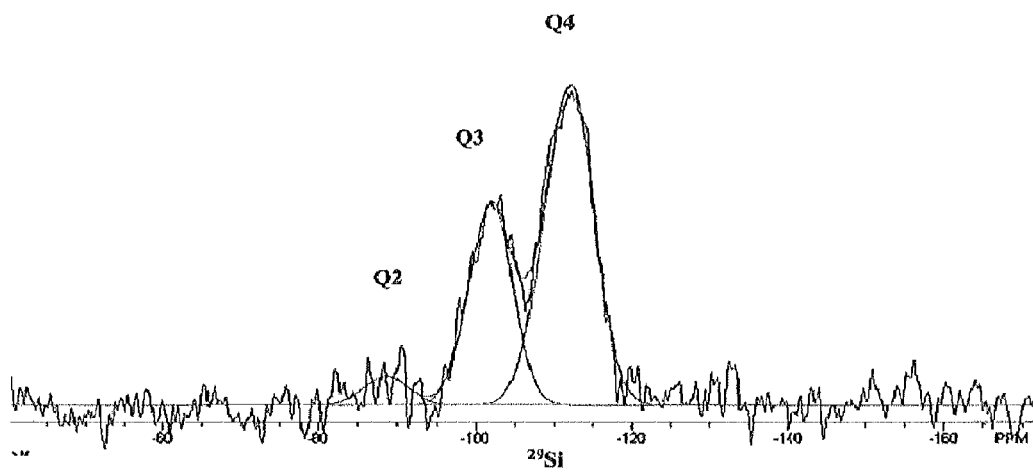
FIG. 2 is an NMR spectrum of a silica microcapsule which has not been post-treated, which spectrum has been deconvoluted to quantify Si—O—Si interactions.

The deconvoluted spectrum for Example 1 is presented in FIG. 1; and that of Comparative Experiment A is presented in FIG. 2. It is noted that peaks Q3(Al)—believed to correspond to Si(OAl)(OH)(OSi)$_3$—and Q4(Al)—corresponding to Si(OAl)(OSi)$_3$—are present in the spectrum for Example 1 but are not present in Comparative Experiment A. Peaks Q2 (corresponding to Si(OH)$_2$(OSi)$_2$), Q3 (corresponding to Si(OH)(OSi)$_3$) and Q4 (corresponding to Si(OSi)$_4$) are present in both spectra.

Example 2

Alumina Post-Treatment of Silica Capsules Containing Chlorpyrifos and Capsule Suspension Formulation Thereof a) Preparation of Silica Capsules Containing Chlorpyrifos Into a 15 liter, jacketed mixing vessel fitted with an agitator blade and an in-line homogenizer, were added 242.1 grams of 25% cetyltrimethyl ammonium chloride and 5,810.6 grams of deionized water. The mixture was stirred with a mechanical stirrer and heated to 40° C.

Into a second 15 liter, jacketed mixing vessel were added 476.7 grams of refined paraffinic petroleum oil (Sunspray® 6N, available from Sunoco, Inc) and 158.9 grams of heavy aromatic naphtha (Aromatic 200, available from ExxonMobile Chemical Company). The contents of the second mixing vessel was stirred with a mechanical stirrer and heated to 40° C. Once at 40° C., 27.2 grams of warm (50° C.) epoxidized soybean oil was added followed by 12.1 grams of octanal, 907.9 grams of tetraethyl orthosilicate and 1,443.1 grams of warm (50° C.) chlorpyrifos technical (95.0% purity). This mixture was stirred until uniform.

The contents of the second vessel were added slowly to the first vessel with continued stirring Once the addition was complete, an in-line homogenizer was turned on and set for 6000 RPM, circulating the mixture through the homogenizer. Homogenization was continued until 90% of the particles (D90) were less than 8 microns. A 1N hydrochloric acid solution (3.03 grams) was diluted with 6,050.2 grams of deionized water and the dilute acid was added to the first mixing vessel. The resultant mixture stirred at 40° C. for about 19 hours. The mixture was cooled to about 25° C. and was transferred to a Sorval RC3C centrifuge and centrifuged at 3500 RPM for 30 minutes. The supernatant was removed yielding 2,690.8 grams of silica encapsulated chlorpyrifos as a wet cake.

b) Alumina Treated Silica Capsules Containing Chlorpyrifos

Into a mixing vessel fitted with a Cowles blade agitator were added 2,690.8 grams of the silica encapsulated chlorpyrifos prepared in Step a, 1,153.5 grams of deionized water and 19.1 grams of sodium decyl sulfate (Polystep® B-25 available from Stepan Corporation). The mixture was stirred with the agitator blade until the slurry was uniform. The agitator blade was removed and replaced with a Silverson batch homogenizer. The homogenizer speed was gradually increased to a speed of 1200 RPM. An aqueous 3% aluminum sulfate solution, 769.0 grams, was added slowly, and after complete addition, homogenization was continued for about 1 minute. The mixture was transferred to a mixing vessel affixed with an agitator blade and was stirred for 15 minutes. A mixture of 38.2 grams of polyvinyl alcohol solution (Celvol® 24-203, available from Sekisui Specialty Chemicals) mixed with 77.0 grams of deionized water was added slowly and after complete addition, the mixture was stirred for about 15 minutes. The agitator blade was replaced with the batch homogenizer. An aqueous 28% sodium silicate solution, 153.9 grams, was added very slowly while maintaining good agitation with the homogenizer. After complete addition, homogenization was continued for 1 minute. The homogenizer was removed and replaced with an agitator blade, and the mixture was stirred for about 3 hours. The resultant slurry provided 4,650.0 grams of alumina treated silica capsules containing chlorpyrifos. A sample of the slurry was analyzed by HPLC and found to contain 26.8% chlorpyrifos (wt %).

c) Capsule Suspension Formulation of Alumina Treated Silica Capsules Containing Chlorpyrifos Into a mixing vessel, affixed with a mechanical stirrer, were added 4,650.0 grams of the slurry prepared in Step b, a solution of 37.5 grams of polyvinylpyrrolidone (PVP K-30 available from ISP Corp.) dissolved in 112.5 grams of deionized water 168.3 grams of tristyrylphenol ethoxylate, potassium salt (Soprophor® FLK, available from Rhodia Novecare), 140.2 grams of acrylic graft co-polomer (Atlox™ 4913 available from Cruda Chemicals, Inc.) and 140.2 grams of glycerine, assuring to stir well between the addition of each ingredient. A solution of 8.0 grams of xanthan gum and 2.0 grams of biocide (Proxel™ GXL, available from Arch Chemicals) dissolved in 390.0 grams of water was prepared and 140.2 grams of this solution was added to the mixture. The mixture was stirred for 3 hours and 140.2 grams of glycerin, 146.2 grams of the xanthan gum/biocide solution and 200 grams of deionized water were added. The resultant capsule suspension formulation was stirred until all ingredients were well dispersed, yielding 5831.5 grams of the final alumina treated silica capsules containing chlorpyrifos formulation. A sample of the formulation was analyzed by HPLC and found to contain 22.7% chlorpyrifos (wt %). The formulation was packaged into plastic containers and the containers sealed for further use.

Comparative Experiment B a) Preparation of Silica Capsules Containing Chlorpyrifos Into a 5 liter mixing vessel, fitted with a mechanical stirrer, were added 1,200.0 grams of an aqueous 1% cetyltrimethyl ammonium chloride solution. The solution was stirred at room temperature.

Into a 3 liter mixing vessel, fitted with a mechanical stirrer, were added 94.5 grams of refined paraffinic petroleum oil (Sunspray® 6N, available from Sunoco, Inc) and 31.5 grams of heavy aromatic naphtha (Aromatic 200, available from ExxonMobil Chemical Company), 5.4 grams of epoxidized soybean oil, 2.4 grams of octanal, 180.0 grams of tetraethyl orthosilicate and 286.2 grams of warm (50° C.) chlorpyrifos technical (95.0% purity). This mixture was stirred until uniform.

The contents of the second vessel were added slowly to the first vessel with continued stirring. Once the addition was complete the mixture was homogenized for 1.5 minutes at 6500 RPM using a Polytron 6100 high-shear mixer. A particle size of less than 8 microns at D 90 was achieved. The mixture was transferred to a jacketed, 5 liter reactor vessel fitted with an overhead mechanical stirrer, warming the stirring mixture to 40° C. With continued stirring, 1,200.0 grams of a 0.0005N hydrochloric acid solution was added. Upon complete addition, the resultant mixture stirred at 40° C. for about 20 hours. The mixture was cooled to about 25° C. and was transferred portion wise into centrifuge bottles and centrifuged at 3500 RPM for 30 minutes. The supernatant was removed from each centrifugation, collecting the silica encapsulated chlorpyrifos as a wet cake for a total of 517.8 grams.

b) Capsule Suspension Formulation of Silica Capsules Containing Chlorpyrifos

Into a mixing vessel, affixed with a mechanical stirrer, were added 35.0 grams of the cake prepared in Step a and 8.75 grams of an aqueous 5% polyvinylpyrrolidone solution. This mixture was stirred until a uniform slurry was obtained.

Into a second mixing vessel, affixed with a mechanical stirrer, were added 32.6 grams of the above slurry, 0.82 gram of polyvinylpyrrolidone (PVP K-30 available from ISP Corp.), 0.63 gram of acrylic graft co-polomer (Atlox™ 4913 available from Croda Chemicals, Inc.) and 3.15 grams of glycerine, assuring to stir well between the addition of each ingredient. A solution of 8.0 grams of xanthan gum and 2.0 grams of biocide (Proxel™ GXL, available from Arch Chemicals) dissolved in 390.0 grams of water was prepared and 3.15 grams of this solution was added to the mixture. Deionized water (21.46 grams) was added and the resultant capsule suspension formulation was stirred until all ingredients were well dispersed, yielding 63.09 grams of the final formulation. A sample of the formulation was analyzed by HPLC and found to contain 21.2% chlorpyrifos (wt %). The formulation was packaged into a plastic container for further use.

Biological Assay of Encapsulated Chlorpyrifos Formulations

The test formulations of encapsulated chlorpyrifos from Example 2 and Comparative Experiment B were diluted in deionized water to provide an application rate of 560 gm ai/ha when applied at a spray volume of 280.5 L/ha. Pinto bean plants were grown in three inch plastic pots in Metro-Mix 360 potting mix, available from Sun Gro Horticulture Canada Ltd., one plant per pot. The pinto bean plants were transferred to a green house and watered daily. About 12 days after planting the plant leaves were of sufficient size to be sprayed; sixteen pinto bean plants were sprayed for each of the formulations using an Allen traveling boom sprayer, calibrated to deliver 280.5 L/ha at 40 to 44 psi, using a hollow cone spray tip. The treated plants were transferred to a hood where they were kept until the leaves had dried. The dry plants were transferred to growth chamber and maintained at 30° C., 50% humidity, with a photo-period of 16 hours light and 8 hours dark and watered by subsurface irrigation until needed for testing at 3, 7, 10 and 14 days after treatment (DAT).

In tests against beet atmyworm (*Spodoptera exigua*), twenty leaf discs (one inch in diameter) were cut from the treated pinto bean plants and each disc placed into a separate (50×9 mm) plastic Petri dish, containing a water-moistened filter paper. Two second-instar beat armyworms were placed into each Petri dish, taking care not to cause injury. The plastic lids were placed on each of the dishes, which were then held for 72 hours at 25° C., 50% relative humidity with a photo-period of 12 hours light and 12 hours dark. At the end of the 72 hour exposure period, the dishes were opened, and the numbers of dead, moribund and live insects were counted. Insects were classified as "moribund" if they showed evidence of restricted movement or could not remain upright. Using the insect counts, the activity of the test chemical was expressed in percent control. Percent control is derived from the total number of dead and moribund insects (TD) compared to the total number of insects (TI) in the test:

$$\% \text{ Control} = \frac{TD}{TI} \times 100.$$

Table 1 below summarizes the % control of beet armyworm larvae with formulations of aluminum cross-linked silica capsules containing chlorpyrifos and silica capsules containing chlorpyrifos.

TABLE 1

Control of Beet Armyworm with Chlorpyrifos Formulations

| Treatment | Rate (gm ai/ha) | % Beet Armyworm Control | | | |
|---|---|---|---|---|---|
| | | 3 DAT | 7 DAT | 10 DAT | 14 DAT |
| Example 2 | 560 | 100 | 100 | 100 | 100 |
| Comparative Experiment B | 560 | 100 | 100 | 94 | 19 |

As can be seen from Table 1, the formulation of silica capsules containing chlorpyrifos began to lose insecticidal effectiveness at ten days after treatment and good insecticidal control was lost by 14 days after treatment whereas the formulation of alumina treated capsules containing chlorpyrifos exhibited complete insecticidal control at both 10 days after treatment and 14 days after treatment.

Example 3 a) An organic phase was prepared by first combining 94.5 g of Sunspray 6N with 31.5 g of Aromatic 200. To this was added 180.0 g of tetraethylorthosilicate, 2.4 g of 1-octanal, 4.4 g of epoxidized soybean oil, and 286.2 g of molten chlorpyrifos technical. An aqueous phase was prepared by dissolving 48.0 g of a 25% aqueous solution of hexadecyltrimethylammonium chloride (CTAC) in 1152.0 g of deionized water. The organic phase was slowly poured into the aqueous phase while being stirred. The crude emulsion was homogenized by blending at 6500 rpm using a Polytron 6100 high-shear mixer so that 90% of the particles (D90) were smaller than 7.7 μm. Formation of the silica shell was initiated by adding 1200 g of 0.0005 N hydrochloric acid. The mixture was stirred for 24 hours while maintaining the temperature of the reaction mixture at 40° C. A wet cake (517.8 g) comprising water and chlorpyrifos-silica microcapsules was obtained after centrifugation of the mixture and was shown to contain 43.0% chlorpyrifos.

b) Microcapsules from step a), 35.64 g, were stirred into 14.46 g of deionized water until a uniform fluid slurry was obtained. To this was added, in order, 0.28 g of Polystep B25, 9.98 g of 3% aluminum sulfate solution, 2.05 g of 28% sodium silicate solution, 0.46 g of polyvinyl alcohol solution, and 1.00 g of deionized water, stirring between each addition until uniform. The mixture was stirred for three hours at room temperature after the final addition. The treated microcapsule product was found to contain 30.6% chlorpyrifos.

c) A formulation was prepared by adding to 5.01 g of the treated microcapsule product from step b) the following ingredients in order, stirring between additions: 0.26 g of 25% polyvinylpyrrolidone solution, 0.08 g of Polystep B25, 0.06 g of Atlox 4913, 0.07 g of Soprophor FLK, 0.33 g of glycerine, 0.31 g of a 0.25% xanthan gum plus 0.10% Proxel GXL dispersion, and 0.62 g of water. The final product contained 20.3% chlorpyrifos with a D90 of 10.4 μm.

Example 4 a) An organic phase was prepared by first combining 94.57 g of Sunspray 6N with 31.58 g of Aromatic 200. To this was added 180.12 g of tetraethylorthosilicate, 2.39 g of 1-octanal, 5.46 g of epoxidized soybean oil, and 287.20 g of molten chlorpyrifos technical. An aqueous phase was prepared by dissolving 48.14 g of a 25% aqueous solution of hexadecyltrimethylammonium chloride (CTAC) in 1152.0 g of deionized water. The organic phase was slowly poured into the aqueous phase while being stirred. The crude emulsion was homogenized by blending at 6500 rpm using a Polytron 6100 high-shear mixer so that 90% of the particles (D90) were smaller than 3.7 μm. Formation of the silica shell was initiated by adding 1200 g of 0.0005 N hydrochloric acid. The mixture was stirred for 24 hours while maintaining the temperature of the reaction mixture at 40° C. A wet cake (513 g) comprising water and chlorpyrifos-silica core-shell capsules was obtained after centrifugation of the mixture and was shown to contain 38.6% chlorpyrifos.

b) Chlorpyrifos-silica core-shell capsules from step a), 50.00 g, were stirred into 21.43 g of deionized water until a uniform fluid slurry was obtained. To this was added, in order, 0.36 g of Polystep B25, 11.43 g of 2.83% zinc sulfate solution, 2.14 g of 33% aqueous polyvinyl alcohol solution, and 2.86 g of 14% sodium silicate solution, stirring after each addition until uniform. The mixture was stirred for three hours at room temperature after the final addition. The treated microcapsule product was found to contain 28.4% chlorpyrifos.

c) A formulation was prepared by adding to 75 g of the treated microcapsule product from step b) the following ingredients in order, stirring between additions: 1.92 g of polyvinylpyrrolidone solution (K-30 solution); 2.40 g of Atlox 4913; 2.88 g of Soprophor FLK; 4.80 g of glycerine; 4.80 g of 0.50% Proxel+2.0% Kelzan; 0.96 g of sodium tripolyphosphate and 3.2 g of water. The final product contained 23.5% chlorpyrifos with a D90 of 4.0 µm.

Example 5 a) 50.00 g of chlorpyrifos microcapsule product (produced by the method described in Example 3a above), were stirred by hand into 21.43 g of deionized water containing 0.36 g of Polystep B25 until a uniform fluid slurry was obtained. To this was added, in order, 11.43 g of 2.83% iron (II) chloride solution, and 2.14 g of 33% aqueous polyvinyl alcohol solution, while stirring after each addition until uniform, employing a Cowles dissolver at a speed of 700 rpm, 2.86 g of 14% sodium silicate solution was added and the mixture was mixed for two hours at room temperature employing a Cowles dissolver at a speed of 1000 rpm. The treated microcapsule product was found to contain 30.7% chlorpyrifos.

b) A formulation was prepared by adding to 75 g of the treated microcapsule product from step a) the following ingredients in order, stirring between additions: 2.07 g of polyvinylpyrrolidone solution (K-30 solution); 2.59 g of Atlox 4913; 3.00 g of Soprophor FLK; 5.19 g of glycerine; 5.19 g of 0.50% Proxel+2.0% Kelzan; 1.04 g of sodium tripolyphosphate and 9.53 g of water. The final product contained 21.35% chlorpyrifos with a D90 of 3.83 µm.

Example 6 a) 50.00 g of chlorpyrifos microcapsule product (produced by the method described in Example 3a above), were stirred by hand into 21.43 g of deionized water containing 0.36 g of Polystep B25 until a uniform fluid slurry was obtained. To this was added, in order, 11.43 g of 1.08% Boric Acid; 2.14 g of 33% aqueous polyvinyl alcohol solution; and 2.86 g of 14% sodium silicate; with the mixture being stirred after each addition until uniform. The treated microcapsule product was found to contain 30% chlorpyrifos.

b) A formulation was prepared by adding to 73 g of the treated microcapsule product from step a) the following ingredients in order, stirring between additions: 1.97 g of polyvinylpyrrolidone solution (K-30 solution); 2.47 g of Atlox 4913; 2.96 g of Soprophor FLK; 4.93 g of glycerine; 4.93 g of 0.50% Proxel+2.0% Kelzan; 0.99 g of sodium tripolyphosphate and 7.40 g of water. The final product contained 22.25% chlorpyrifos with a D90 of 86.88 µm.

Example 7 a) 50.00 g of chlorpyrifos microcapsule product (produced by the method described in Example 3a above), were stirred by hand into 21.43 g of deionized water containing 0.36 g of Polystep B25 until a uniform fluid slurry was obtained. To this was added, in order, 11.43 g of 2.3% aluminum chloride; 2.14 g of 33% aqueous polyvinyl alcohol solution; and 2.86 g of 14% sodium silicate; with the mixture being stirred after each addition until uniform. The treated microcapsule product was found to contain 27.9% chlorpyrifos.

b) A formulation was prepared by adding to 75 g of the treated microcapsule product from step a) the following ingredients in order, stirring between additions: 1.89 g of polyvinylpyrrolidone solution (K-30 solution); 2.36 g of Atlox 4913; 2.83 g of Soprophor FLK; 4.71 g of glycerine; 4.71 g of 0.50% Proxel 1-2.0% Kelzan; 0.94 g of sodium tripolyphosphate and 1.82 g of water. The final product contained 23.35% chlorpyrifos with a D90 of 3.97 µm.

Example 8 a) 50.00 g of chlorpyrifos microcapsule product (produced by the method described in Example 3a above), were stirred by hand into 21.43 g of deionized water containing 0.36 g of Polystep B25 until a uniform fluid slurry was obtained. To this was added, in order, 11.43 g of 3.8% aluminum nitrate; 2.14 g of 33% aqueous polyvinyl alcohol solution; and 2.86 g of 14% sodium silicate; with the mixture being stirred after each addition until uniform. The treated microcapsule product was found to contain 28.2% chlorpyrifos.

b) A formulation was prepared by adding to 74 g of the treated microcapsule product from step a) the following ingredients in order, stirring between additions: 1.88 g of polyvinylpyrrolidone solution (K-30 solution); 2.35 g of Atlox 4913; 2.82 g of Soprophor FLK; 4.70 g of glycerine; 4.70 g of 0.50% Proxel+2.0% Kelzan; 0.94 g of sodium tripolyphosphate and 2.61 g of water. The final product contained 23.15% chlorpyrifos with a D90 of 4.065 µm.

Example 9 a) An organic phase was prepared by combining 21 g of Aromatic 200; 30 g of tetraethylorthosilicate; and 49 grams of carfentrazone-ethyl. An aqueous phase was prepared by dissolving 8 g of a 25% aqueous solution of hexadecyltrimethylammonium chloride (CTAC) in 192 g of deionized water. The organic phase was slowly poured into the aqueous phase while being stirred to form a crude emulsion having a D90 of 2.875 µm. Formation of the silica shell was initiated by adding 200 g of 0.0005 N hydrochloric acid. The mixture was stirred until polymerization was complete. A wet cake (87.2 g) comprising water and carfentrazone-ethyl microcapsules was obtained after centrifugation of the mixture.

b) 80.00 g of the carfentrazone-ethyl wet cake produced in step a) were stirred by hand into 34.29 g of deionized water containing 0.57 g of Polystep B25 until a uniform fluid slurry was obtained. To this was added, in order, 18.29 g of 3% aluminum sulfate; 3.43 g of 33% aqueous polyvinyl alcohol solution; and 4.68 g of 14% sodium silicate; with the mixture being stirred after each addition until uniform. The treated microcapsule product was found to contain 28.2% carfentrazone-ethyl.

c) A formulation was prepared by adding to 127.50 g of the treated microcapsule product from step a) the following ingredients in order, stirring between additions: 3.60 g of polyvinylpyrrolidone solution (K-30 solution); 4.49 g of Atlox 4913; 5.39 g of Soprophor FLK; 8.99 g of glycerine;

8.99 g of 0.50% Proxel+2.0% Kelzan; 1.80 g of sodium tripolyphosphate and 19.02 g of water. The final product contained 19.9% carfentrazone-ethyl with a D90 of 4.849 µm.

Example 10 a) An organic phase was prepared by combining 21 g of Aromatic 200; 30 g of tetraethylorthosilicate; and 49 grams of bifenthrin. An aqueous phase was prepared by dissolving 8 g of a 25% aqueous solution of hexadecyltrimethylammonium chloride (CTAC) in 192 g of deionized water. The organic phase was slowly poured into the aqueous phase while being stirred to form a crude emulsion having a D90 of 3.152 µm. Formation of the silica shell was initiated by adding 200 g of 0.0005 N hydrochloric acid. The mixture was stirred until polymerization was complete. A wet cake (88 g) comprising water and bifenthrin microcapsules was obtained after centrifugation of the mixture.

b) 80.00 g of the bifenthrin wet cake produced in step a) were stirred by hand into 34.29 g of deionized water containing 0.57 g of Polystep B25 until a uniform fluid slurry was obtained. To this was added, in order, 18.29 g of 3% aluminum sulfate; 3.43 g of 33% aqueous polyvinyl alcohol solution; and 4.57 g of 14% sodium silicate; with the mixture being stirred after each addition until uniform. The treated microcapsule product was found to contain 27.7% bifenthrin.

c) A formulation was prepared by adding to 125.00 g of the treated microcapsule product from step b) the following ingredients in order, stirring between additions: 3.46 g of polyvinylpyrrolidone solution (K-30 solution); 4.33 g of Atlox 4913; 5.19 g of Soprophor FLK; 8.66 g of glycerine; 8.66 g of 0.50% Proxel+2.0% Kelzan; 1.73 g of sodium tripolyphosphate and 16.10 g of water. The final product contained 20.8% bifenthrin with a D90 of 3.727 µm.

Example 11 a) An organic phase was prepared by combining 52.50 g of Aromatic 200; 30.00 g of tetraethylorthosilicate; and 17.50 grams of 95% tebuconazole. An aqueous phase was prepared by dissolving 8 g of a 25% aqueous solution of hexadecyltrimethylammonium chloride (CTAC) in 192 g of deionized water. The organic phase was slowly poured into the aqueous phase while being stirred to form a crude emulsion having a D90 of 1.597 µm. Formation of the silica shell was initiated by adding 200 g of 0.0005 N hydrochloric acid. The mixture was stirred until polymerization was complete. A wet cake comprising water and tebuconazole microcapsules was obtained after centrifugation of the mixture.

b) 98.00 g of the tebuconazole wet cake produced in step a) were stirred by hand into 42.00 g of deionized water containing 0.70 g of Polystep B25 until a uniform fluid slurry was obtained. To this was added, in order, 22.40 g of 3% aluminum sulfate; 4.20 g of 33% aqueous polyvinyl alcohol solution; and 5.71 g of 14% sodium silicate; with the mixture being stirred after each addition until uniform. The treated microcapsule product was found to contain 9.3% tebuconazole.

c) A formulation was prepared by adding to 140.00 g of the treated microcapsule product from step a) the following ingredients in order, stirring between additions: 3.44 g of polyvinylpyrrolidone solution (K-30 solution); 4.30 g of Atlox 4913; 5.16 g of Soprophor FLK; 8.60 g of glycerine; 8.60 g of 0.50% Proxel+2.0% Kelzan; 1.72 g of sodium tripolyphosphate and 0.18 g of water. The final product contained 7.1% tebuconazole with a D90 of 3.329 µm.

Example 12 a) An organic phase was prepared by combining 25 g of Aromatic 200; 20 g of tetraethylorthosilicate; 1.3 g Agrimer AL22; 62.5 g of pendimethalin; and sonicated for 20 minutes to insure complete dissolution. An aqueous phase was prepared by dissolving 3.5 g of a 25% aqueous solution of hexadecyltrimethylammonium chloride (CTAC) and 2.0 g Celvol 24-203 in 136 g of deionized water. The aqueous phase was slowly poured into the organic phase while being stirred to form a crude emulsion having a D90 of 12.3 µm. Formation of the silica shell was initiated by adding 0.001 N hydrochloric acid until the emulsion pH was 3.4. The mixture was stirred overnight at 40° C. until polymerization was complete. A wet cake (120 g) comprising water and pendimethalin microcapsules was obtained after centrifugation of the mixture.

b) 28.0 g of the pendimethalin wet cake produced in step a) were stirred by hand into 12 g of deionized water containing 0.2 g of Polystep B25 until a uniform fluid slurry was obtained. To this was added, in order, 2.4 g of 6% aluminum sulfate; 1.2 g of 33% aqueous polyvinyl alcohol solution; and finally slow addition of 1.6 g of 14% sodium silicate; with the mixture being stirred after each addition until uniform. The treated microcapsule product was found to contain 30.9% pendimethalin c) A formulation was prepared by adding to 125.00 g of the treated microcapsule product from step b) the following ingredients in order, stirring between additions: 4.4 g of a 25% aqueous polyvinylpyrrolidone solution (K-30 solution); 0.55 g of Atlox 4913; 1.66 g of Soprophor FLK; 2.74 g of glycerine; 2.75 g of 0.50% Proxel+2.0% Kelzan; 0.55 g of sodium tripolyphosphate and 5.0 g of deionized water. The final product contained 20.8% pendimethalin with a D90 of 13.15 µm.

Example 13 a) An organic phase was prepared by combining 101.15 g of 2,4-D ethyl hexyl ester technical and 17.85 g of corn oil. To this was added 51 g of tetraethylorthosilicate, An aqueous phase was prepared by dissolving 17.0 g of a 25% aqueous solution of hexadecyltrimethylammonium chloride (CTAC) in 153.0 g of deionized water. The organic phase was slowly poured into the aqueous phase while being stirred. The crude emulsion was homogenized by blending at 5500 rpm using a Polytron 6100 high-shear mixer so that 90% of the particles (D90) were smaller than 10 µm. Formation of the silica shell was initiated by adding 509 g of 0.0005 N hydrochloric acid. The mixture was stirred for 24 hours while maintaining the temperature of the reaction mixture at 45° C. A wet cake comprising water and 2,4-D EHE-silica microcapsules was obtained after centrifugation of the mixture.

b) 16.90 g of the above 2,4-D EHE microcapsule product, were stirred by hand into 3.31 g of deionized water containing 0.17 g of 20% Reax 88A until a uniform fluid slurry was obtained. To this was added, in order, 0.87 g of 10% aluminum sulfate; 2.39 g of 10% aqueous polyvinyl alcohol solution; and 1.35 g of 10% sodium silicate; with the mixture being stirred after each addition until uniform.

c) A formulation was prepared by adding to 13.64 g of the treated microcapsule product from step b) the following ingredients in order, stirring between additions: 1.0 g of polyvinylpyrrolidone solution (40% K-30 solution); 2.0 g of Reax 88A; 1.0 g of Atlox 4913; 1.21 g of glycerine; 1.0 g of 0.50% Proxel+2.0% Kelzan. The final product contained 28.4% 2,4-D EHE with a D90 of 7.6 μm.

Example 14 a) An organic phase was prepared by combining 120.0 g of clomazone, 60.0 g of tetraethylorthosilicate and 15 g of epoxidized soybean oil. An aqueous phase was prepared by dissolving 3.0 g of a 25% aqueous solution of hexadecyltrimethylammonium chloride (CTAC) in 300.0 g of deionized water. The organic phase was slowly poured into the aqueous phase while being stirred. The crude emulsion was homogenized using a Waring Blender, so that 90% of the particles (D90) were smaller than 10 μm. Formation of the silica shell was initiated by adding a few drops of acetic acid to pH 3.0-3.5. The mixture was stirred at room temperature for 24 hours.

b) 52.00 g of clomazone microcapsule mixture produced in step a) (24% loading) were stirred mechanically and 2 g of 40% aluminum sulfate was added drop wise. 1.5 g of 28% sodium silicate and 5 g of 40% polyvinylpyrrolidone solution (K-30 solution) was added subsequently. Another 1.7 g of 28% sodium silicate was added and the mixture stirred until uniform.

What is claimed is:

1. A microcapsule comprising a core material comprising an active ingredient encapsulated within a silica shell; said silica shell being modified by post-treatment with an inorganic metal salt or acid selected from Group 2a, Group 8, Group 2b and Group 3a metal salt and acid thereof wherein the outer surface of said silica shell has bound thereto a layer consisting of a metal selected from the group consisting of Group 2a, Group 8, Group 2b, and Group 3a metals.

2. The microcapsule of claim 1 wherein the active ingredient is a pesticide.

3. The microcapsule of claim 1 wherein the metal is selected from the group consisting of magnesium, calcium, iron, cobalt, nickel, aluminum and boron.

4. The microcapsule of claim 3 wherein the metal is aluminum.

5. The microcapsule of claim 2 wherein the pesticide is an herbicide.

6. The microcapsule of claim 5 wherein the herbicide is selected from the group consisting of Acetochlor, Aclonifen, Alachlor, Anilofos, Asulam, Benfluralin, Benfuresate, Bensulide, Benzoylprop-ethyl, Bromoxynil, Butachlor, Butenachlor, Butralin, Carfentrazone-ethyl, Chlorbufam, Chlorfenprop-methyl, Chlorpropham, Clodinafop-propargyl, Clofop-isobutyl, Clomazone, Cloquintocet-methyl, Cycloxydim, Cyometrinil, Di-allate, Diclofop-methyl, Diethatyl-ethyl, Diflufenican, Dimepiperate, Dimethachlor, Dimethametrin, Dimethenamid-P, Dinoseb, Ethalfluralin, Ethofumesate, Ethoxysulfuron, Fenoxaprop, Fenthiaprop-ethyl, Fentrazamide, Fluazifop-butyl, Fluazifop-P-butyl, Fluchloralin, Fluoroglycophen-ethyl, Fluorochloridone, Fluoroxypyr-methyl, Haloxyfop-P-methyl, Idosulfuron, Ioxynil Octanoate, Lactofen, MCPB-ethyl, Mesotrione, Methoxyphenone, Metolachlor, Metribuzin, Nitrofen, Nonanoic Acid, Orbincarb, Oxadiazon, Pendimethalin, Pethoxamid, Phenmedipham, Pinoxaden, Propaquizafop, Propischlor, Pyridate, Pyriftalid, Quinoline, Quizalofop-tefuryl, S-metolachlor, Thiobencarb, Tri-allate, Tridifane, Trifloxysulfuron sodium, Trifluralin and mixtures thereof.

7. The microcapsule of claim 2 wherein the pesticide is an insecticide.

8. The microcapsule of claim 7 wherein the insecticide is selected from the group consisting of Abamectin, Aldicarb, Aldrin, Alpha-cypermethrin, Avermectin, Azinphos-ethyl, Beta-cyfluthrin, Beta-cypermethrin, Bifenthrin, Bioremethrin, Bromophos, Bufencarb, Buprofezin, Carbofuran, Carbaryl, Chlorfenvinphos, Chlorphoxim, Chlorpyrifos, Chlorpyriphos-methyl, Clofentezine, Cyfluthrin, Cypermethrin, Cyromazine, DDVP, Deltamethrin, Diafenthiuron, Dialifos, Diazinon, Dicofol, Dimethoate, Dimethomorph, Dimethylvinphos, Dioxabenzofos, Disulfoton, Emamectin benzoate, EPN, Endosulfan, Esfenvalerate, Ethiofencarb, Etofenprox, Fenamiphos, Fenchlorphos, Fenitrothion, Fenobucarb, Fenoxycarb, Fenpropathrin, Fensulfothion, Fenvalerate, Fipronil, Flufenoxuron, Fosmethilan, Fosthiazate, Gamma-cyhalothrin, Imidacloprid, Isoprocarb, Ivermectin, Lambda-cyhalothrin, Lufenuron, Malathion, Mecarphon, Methamidofos, Methidathion, Methomyl, Metolcarb, Monocrotophos, Niclosamide, Novaluron, Parathion, Permethrin, Phenthoate, Phorate, Phoxim, Pirimiphos-ethyl, Pirimicarb, Profenofos, Propoxur, Prothoate, Pymetrozin, Sulprofos, Tetramethrin, Thiamethoxam, Thiacloprid, Thiodicarb, Thionazin, Transfluthrin, Triazamate, Tribufos, Triflumuron, Zeta-cypermethrin and mixtures thereof.

9. The microcapsule of claim 2 wherein the pesticide is a fungicide.

10. The microcapsule of claim 9 wherein the fungicide is selected from the group consisting of Aldimorph, Azoxystrobin, Binapacryl, Buthiobate, Captan, Chlorothalonil, Cyflufenamid, Cyproconazole, Difenoconazole, Diflumetorim, Dinobuton, Dinocap, Dedemorph acetate, Edifenphos, Epoxiconazole, Etridiazole, Fenamidon, Fenpropimorph, Fenitropan, Flusilazole, Folpet, Furalaxyl, Furmecyclox, Imazalil, Isoprothiolane, Kresoxim-methyl, Mefenoxam, Metominostrobin, Nitrothal-isopropyl, Penconazole, 2-Phenylphenol, Propiconazole, Prochloraz, Proquinazid, Prothioconazole, Pyraclostrobin, Pyrazophos, Pyrimethanil, Qyprodinil, Tebuconazole, Tetraconazole, Thiabendazole, Triadiminol, Trifloxystrobin Triticonazole and mixtures thereof.

11. The microcapsule of claim 2, wherein the metal is aluminum.

12. A process for making the microcapsule of claim 1 comprising:
    a) encapsulating the core material in the silica shell employing a sol gel polymerization process to form a microcapsule; and
    b) treating the microcapsule with an acid or salt of a metal selected from the group consisting of Group 2a, Group 8, Group 2b and Group 3a metals of the Periodic Table.

13. A pesticidal composition comprising:
    a) a treated microcapsule comprising an active ingredient which is a pesticide; and
    b) a carrier;
    wherein the treated microcapsule comprises a core material comprising an active ingredient encapsulated within a silica shell;
    said silica shell being modified by post-treatment with an inorganic metal salt or acid selected from Group 2a, Group 8, Group 2b and Group 3a metal salt and acid thereof wherein the outer surface of said silica shell has bound thereto a layer of a metal selected from the group consisting of Group 2a, Group 8, Group 2b , and Group 3a metals.

14. A method of controlling pests comprising applying an effective amount of the pesticidal composition of claim 13 to a locus where pests are or are expected to be present.

* * * * *